United States Patent
Cho et al.

(10) Patent No.: US 12,201,430 B2
(45) Date of Patent: Jan. 21, 2025

(54) WEARABLE DEVICE HAVING STRUCTURE PREVENTING MEASUREMENT ERROR CAUSED BY IMPEDANCE

(71) Applicant: ATSENS CO., LTD., Gyeonggi-do (KR)

(72) Inventors: Seung Bum Cho, Gyeonggi-do (KR); Deok Byeong Chae, Gyeonggi-do (KR); Jong Ook Jeong, Gyeonggi-do (KR)

(73) Assignee: ATsens Co., Ltd., Gyeonggi-do (KR)

( * ) Notice: Subject to any disclaimer, the term of this patent is extended or adjusted under 35 U.S.C. 154(b) by 698 days.

(21) Appl. No.: 17/506,335

(22) Filed: Oct. 20, 2021

(65) Prior Publication Data
US 2022/0142544 A1    May 12, 2022

(30) Foreign Application Priority Data

Nov. 6, 2020  (KR) .................. 10-2020-0148141

(51) Int. Cl.
*A61B 5/276* (2021.01)
*A61B 5/00* (2006.01)
*A61B 5/282* (2021.01)

(52) U.S. Cl.
CPC .............. *A61B 5/276* (2021.01); *A61B 5/282* (2021.01); *A61B 5/4839* (2013.01);
(Continued)

(58) Field of Classification Search
CPC ......... A61B 5/257; A61B 5/259; A61B 5/263; A61B 5/276; A61B 5/282; A61B 5/291;
(Continued)

(56) References Cited

U.S. PATENT DOCUMENTS 8,483,809 B2    7/2013 Kim et al.
2017/0164860 A1    6/2017 Hung et al.
(Continued)

FOREIGN PATENT DOCUMENTS

JP    2004167110 A    6/2004
JP    2014008166 A    1/2014
(Continued)

OTHER PUBLICATIONS

Extended European Search Report for European Application No. 21200898.1, mailed Mar. 24, 2022, 8 pages.
(Continued)

*Primary Examiner* — Eun Hwa Kim
(74) *Attorney, Agent, or Firm* — Guntin & Gust, PLC; Miyoung Shin (57) ABSTRACT

The present disclosure relates to a wearable device having a structure that prevents impedance measurement errors. The wearable device, which is used by being attached to the skin of a user, includes a plurality of electrodes spaced apart from each other, conductive members, blocking members, and absorbent members. A conductive member is positioned on one surface of each of the plurality of electrodes and comprises an exposure portion. A blocking member includes a different material from the conductive member and covers an outside of the conductive member so that the exposure portion is present within the blocking member. An absorbent member is positioned in the outside of the blocking member and comes into contact with the skin of the user.

10 Claims, 9 Drawing Sheets

(52) U.S. Cl.
CPC .... *A61B 5/6833* (2013.01); *A61B 2562/0209* (2013.01); *A61B 2562/046* (2013.01); *A61B 2562/18* (2013.01)

(58) Field of Classification Search
CPC ..... A61B 5/296; A61B 5/6802; A61B 5/6832; A61B 5/68335; A61B 2562/18
See application file for complete search history.

(56) References Cited

U.S. PATENT DOCUMENTS

| | | |
|---|---|---|
| 2018/0192911 A1 | 7/2018 | Jung et al. |
| 2019/0290137 A1 | 9/2019 | Zhang et al. |

FOREIGN PATENT DOCUMENTS

| | | | | |
|---|---|---|---|---|
| JP | 2019162417 A | * | 9/2019 | ............. A61B 5/257 |
| KR | 1020090102943 A | | 10/2009 | |
| KR | 20180046868 A | | 5/2018 | |
| WO | 2019204485 A1 | | 10/2019 | |

OTHER PUBLICATIONS

Notice of Allowance issued to corresponding KR Application No. 1020200148141, issued Jan. 19, 2021, 2 pages.

* cited by examiner

WEARABLE DEVICE HAVING STRUCTURE PREVENTING MEASUREMENT ERROR CAUSED BY IMPEDANCE

CROSS-REFERENCE TO RELATED APPLICATION

This application is based on and claims priority under 35 U.S.C. § 119 to Korean Patent Application No. 10-2020-0148141, filed on Nov. 6, 2020, in the Korean Intellectual Property Office, the disclosure of which is incorporated by reference herein in its entirety.

BACKGROUND

1. Field

One or more embodiments relate to a wearable device, and more particularly, to a wearable device having a structure that prevents deterioration of measurement precision by impedance caused by moisture, foreign substances, or the like.

2. Description of the Related Art

Wearable devices are attached to the body of a user such as abdomen, back, shoulder, head, or arm to measure bio signals in regard to an electromyogram, an electrocardiogram, blood pressure, or brain waves. Also, such wearable devices can be used to inject a treatment medicine via an iontophoretic method in the user's body or measure ionic materials (e.g., diabetic materials) present in the user's body. For example, in the case of a wearable device for generating an electrocardiogram, electrodes are attached to the body of a user to come into contact with the skin of the user, and these electrodes can generate an electrocardiogram by sensing the electrical activity of the heart. Due to such characteristics, the wearable device needs to operate while being attached to the body of a user for a long period of time.

However, sweat generated from a user performing various activities while wearing the wearable device or water flowing in from the outside may infiltrate between the skin and may damage electrical isolation between the electrodes of the wearable device. Accordingly, the impedance between electrodes becomes lower, and thus, the quality of a measured signal deteriorates.

The related art described above is technical information possessed to derive the present disclosure or learned in the course of deriving the present disclosure by the inventor, and cannot necessarily be said to be known art published to the general public before filing of the present disclosure.

SUMMARY

One or more embodiments include a wearable device capable of preventing sweat or water flowing in from the outside from infiltrating into or between electrodes, thereby reducing a change in the impedance between electrodes even when the wearable device is worn for a long period of time.

However, these are merely examples, and one or more embodiments are not limited thereto.

Additional aspects will be set forth in part in the description which follows and, in part, will be apparent from the description, or may be learned by practice of the presented embodiments of the disclosure.

According to one or more embodiments, a wearable device, which is capable of being attached to the skin of a user, includes: a plurality of electrodes spaced apart from each other; conductive members, each of which is positioned on one surface of each of the plurality of electrodes and comprises an exposure portion; blocking members, each of which includes a different material from the conductive member and covers the outside of the conductive member so that the exposure portion is present within the blocking member; and absorbent members, each of which is positioned outside of the blocking member and comes into contact with the skin of the user.

In the wearable device according to an embodiment, the absorbent member may include a membrane having a plurality of pores, wherein a size of each of the pores may be greater than a size of each of water particles flowing out from the skin of the user but less than a size of each of water particles flowing from the outside.

In the wearable device according to an embodiment, the blocking member may be positioned concentrically with the conductive member and spaced a first distance from the conductive member to define a discharge region.

In the wearable device according to an embodiment, part of the water flowing out from the skin of the user may flow in the absorbent member, and another part of the water may be discharged to the outside through the discharge region.

In the wearable device according to an embodiment, the conductive member may include a conductive hydrogel.

In the wearable device according to an embodiment, the conductive member may further include a transdermally absorbable drug that has ionic components.

In the wearable device according to an embodiment, the conductive member may further include a chemical substance that contains a transdermally absorbable drug having ionic components.

In the wearable device according to an embodiment, the conductive member may include: a first conductive portion positioned on the one surface of the electrode and having a first outer diameter; and a second conductive portion positioned concentrically with the first conductive portion and having a second outer diameter less than the first outer diameter, wherein the blocking member overlaps at least a portion of the first conductive portion in a first direction.

In the wearable device according to an embodiment, the conductive member may further include a third conductive portion positioned between the first conductive portion and the second conductive portion, at least a portion of the third conductive portion overlapping the blocking member in the first direction, and the first conductive portion may be positioned on a bottom surface of the blocking member and form a different layer from the blocking member.

In the wearable device according to an embodiment, the blocking member may include: a first blocking portion positioned along the outer circumferential surface of the conductive member and overlapping the conductive member in the first direction; and a second blocking portion extending outward from one side of the first blocking portion in a radial direction.

In the wearable device according to an embodiment, the second blocking portion may overlap the absorbent member in the first direction.

In the wearable device according to an embodiment, the absorbent member may be positioned on the second blocking portion and form a different layer from the second blocking portion.

Other aspects, features, and advantages in addition to those described above will be apparent from the following detailed description, claims, and drawings.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Since the present disclosure may be diversely modified and have various embodiments, specific embodiments are exemplified in the drawings and described in detail in the detailed description of the disclosure. However, this is not intended to limit the present disclosure to specific embodiments, and it should be understood that the present disclosure covers all the modifications, equivalents, and replacements within the idea and technical scope of the present disclosure. In the description of the present disclosure, the same components are denoted by the same reference numerals even though illustrated in another exemplary embodiment.

Hereinafter, embodiments of the present disclosure are described in detail with reference to the accompanying drawings, and when describing with reference to the drawings, the identical or corresponding components are given with the same reference numerals, and their duplicated descriptions will be omitted.

In the following embodiments, terms "first" and "second" are used to distinguish one component from another component, but these components should not be limited by these terms.

In the following embodiments, the singular forms include the plural forms as well, unless the context clearly indicates otherwise.

In the following embodiments, the terms "comprises" or "comprising" when used in this specification are to specify the presence of stated features or components, but do not preclude the addition of one or more other features or components.

In the drawings, the dimensions of elements may be exaggerated or downscaled for convenience of description. For example, since the size and thickness of each component shown in the drawings are arbitrarily shown for convenience of description, and the present disclosure is not necessarily limited thereto.

In the following embodiments, the x-axis, the y-axis, and the z-axis are not limited to three axes of the rectangular coordinate system, and may be interpreted in a broader sense. For example, the x-axis, the y-axis, and the z-axis may be perpendicular to one another, or may represent different directions that are not perpendicular to one another.

When a certain embodiment may be implemented differently, a specific process order may be performed differently from the described order. For example, two consecutively described processes may be performed substantially at the same time or performed in an order opposite to the described order.

In the following description, the terms are used only for explaining a specific embodiment and not tend to limit the present disclosure. In the present application, it will be understood that the term "includes" or "comprises", when used in this specification, specifies the presence of stated features, numbers, steps, operations, elements, components, or a combination thereof, but does not preclude the presence or addition of one or more other features, numbers, steps, operations, elements, components, or combinations thereof.

Figure 1:
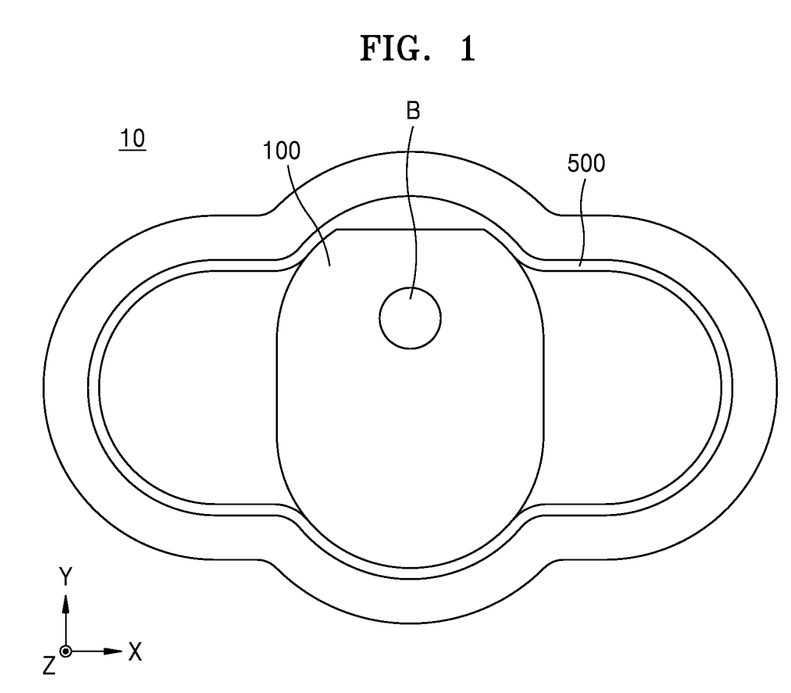
FIG. 1 shows a top surface of a wearable device according to an embodiment.
Figure 2:
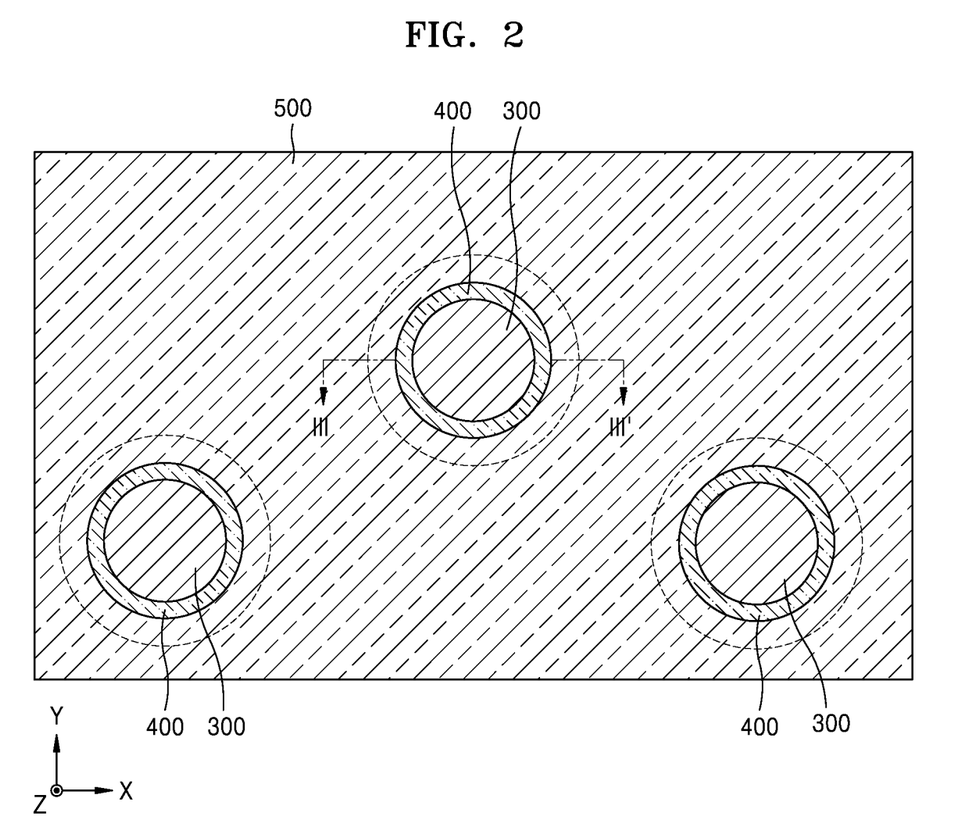
FIG. 2 shows a bottom surface of the wearable device according to an embodiment.
Figure 3:
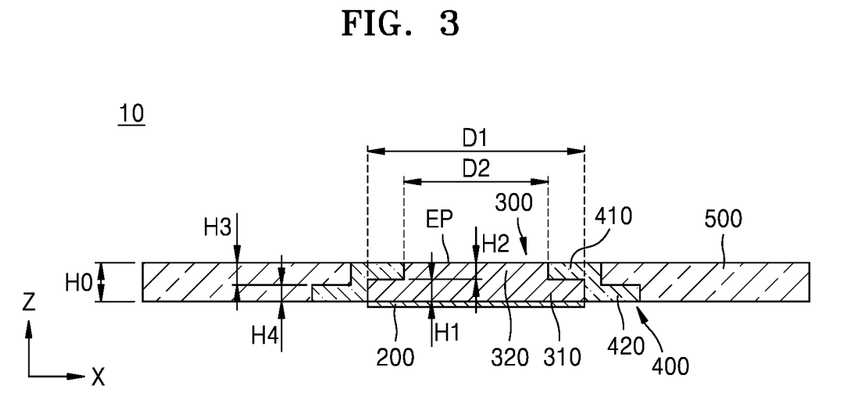
FIG. 3 shows a cross-section of the wearable device taken along line III-III' of FIG. 2.

FIG. 1 shows a top surface of a wearable device 10 according to an embodiment, FIG. 2 shows a part of a bottom surface of the wearable device 10 according to an embodiment, and FIG. 3 shows a cross-section of the wearable device taken along line III-III' of FIG. 2.

The wearable device 10 according to an embodiment may be an electronic device which is attached to the back, chest, shoulder, arm, leg, head, or the like of a user for use. For example, the wearable device 10 according to an embodiment may be a device which is attached to the skin of the user to measure bio signals such as electrocardiogram, electroencephalogram, electromyogram, or blood pressure. In an embodiment, the wearable device 10 may be a device which measures electrocardiogram (ECG) by using an electrode 200 that amplifies electric current generated together with a heartbeat. Also, the wearable device 10 may be a device which measures electroencephalogram (ECG) by using an electrode 200 that amplifies electric current generated when a signal is transmitted between the cranial nerves. Also, the wearable device 10 may be a device which measures electromyogram (EMG) by using an electrode 200 that amplifies electric potential generated in the skeletal muscle. Also, the wearable device 10 may be a continuous glucose monitor (CGM) or a transdermal therapeutic device, which uses iontophoresis on the basis of measured bio signals such as the electrocardiogram, electroencephalogram, or electromyogram.

Referring to FIGS. 1 to 3, the wearable device 10 according to an embodiment may include a housing 100, an electrode 200, a conductive member 300, a blocking member 400, and an absorbent member 500.

The housing 100 forms a frame of the wearable device 10. The housing 100 is provided with an inner space, and components for operating the wearable device 10 may be arranged in the inner space. For example, a PCB board, a battery, a processor, and the like may be arranged in the inner space. These components may be well-known components used to operate the wearable device 10, and detailed description thereof will be omitted.

The housing 100 may have the hardness and strength of a certain level of more to protect the internal components from external impact, scratches, and the like. Also, the housing 100 may be made of a flexible material so that the wearable device 10 is easily attached to the skin of a user.

FIG. 1 shows that a central portion of the housing 100 protrudes and wing portions are arranged on both sides, but the shape of the housing 100 is not specifically limited. For example, the housing 100 may have cuboid or other polyhedron shapes.

A button B may be positioned on one side of the housing 100. FIG. 1 shows that one button B is positioned, but the number of buttons is not specifically limited. The button B may be a power button for operating the wearable device 10 or a button for switching an operation mode.

The electrode 200 may be positioned on one side of the housing 100. For example, as shown in FIG. 3, the electrode 200 is positioned on the bottom surface of the housing 100 and connected to a measurement circuit. Here, the electrode 200 represents a sensing electrode, and may be positioned in the inner space of the housing 100 and connected to a PCB circuit or the like positioned within the housing 100.

In an embodiment, the electrode 200 may measure electric potential on the surface of the body relating to a heartbeat. Also, the electrode 200 may apply electric current so that electrolytic medicine is injected into the body of a user through the skin or mucous membrane.

In an embodiment, at least one or more electrodes 200 may be provided according to the purpose of use and the attachment positions. Also, the plurality of electrodes 200 may be spaced apart from each other. For example, three of the electrodes 200 may be spaced apart from each other on the bottom surface of the housing 100.

The conductive member 300 may be positioned on one surface of the electrode 200. For example, the conductive member 300 is positioned on the surface such that the electrode 200 faces the skin, and may come into direct contact with the skin of the user. The type of the conductive member 300 is not specifically limited and may include a conductive hydrogel as an embodiment. The conductive member 300 is made of a flexible material and may be appropriately deformed to conform to the curve of the skin of the user when coming into contact with the skin, thereby achieving a favorable contact state between the electrode 200 and the skin.

In an embodiment, an exposure portion EP may be provided on the top surface of the conductive member 300. The exposure portion EP is a region which is not covered by the blocking member 400 or the like which will be described later, and may be region which comes into direct contact with the skin of the user.

In an embodiment, the conductive member 300 may include a first conductive portion 310 and a second conductive portion 320.

As shown in FIG. 3, the first conductive portion 310 is positioned on one surface of the electrode 200 and may have a first outer diameter D1. FIG. 3 shows that the first outer diameter D1 is equal to the outer diameter of the electrode 200, but the embodiment is not limited thereto. For example, the first outer diameter D1 may be greater than the outer diameter of the electrode 200, and thus may cover the entire one surface of the electrode 200. On the other hand, the first outer diameter D1 may be less than the outer diameter of the electrode 200, and thus may overlap a portion of the one surface of the electrode 200.

In an embodiment, the first conductive portion 310 may have a height H1 in a first direction (for example, the Z-axis direction of FIG. 3). FIG. 3 shows that the height H1 is greater than a height H4 of a second blocking portion 420, but the embodiment is not limited thereto. For example, the height H1 may be less than or equal to the height H4.

The second conductive portion 320 may be positioned concentrically with the first conductive portion 310 and have a second outer diameter D2 less than the first outer diameter D1. In an embodiment, the exposure portion EP may be provided on one surface of the second conductive portion 320.

In an embodiment, the exposure portion EP may be positioned at the same height as the blocking member 400 and/or the absorbent member 500. That is, as shown in FIG. 3, the surface of the exposure portion EP in contact with the skin of the user may be positioned at the same height as the top surface of the blocking member 400 and/or the absorbent member 500. Accordingly, any one of the exposure portion EP, the blocking member 400, and the absorbent member 500 does not protrude further than the others, and thus, they may uniformly come into contact with the skin of the user.

In an embodiment, the second conductive portion 320 may have a height H2 in the first direction (for example, the Z-axis direction of FIG. 3). FIG. 3 shows that the height H2 is less than a height H3 of a first blocking portion 410, but the embodiment is not limited thereto. For example, the height H2 may be greater than or equal to the height H3.

In an embodiment, the first conductive portion 310 and the second conductive portion 320 may be integrally formed or physically separated from each other.

In an embodiment, the conductive member 300 may further include a transdermally absorbable drug having ionic components. More particularly, in a case where the wearable device 10 is a transdermal therapeutic device that uses iontophoresis, when electric current is applied to the electrode 200, the transdermally absorbable drug may be discharged from the conductive member 300 and then injected through the skin. Here, the transdermally absorbable drug may be glucose or other drugs that may flow in through the skin.

In an embodiment, the conductive member 300 may further include a chemical substance that contains and retains a drug having ionic components. More particularly, the chemical substance contained in the conductive member 300 holds (contains and retains) the drug having ionic components in a normal state, but the drug may be discharged only when constant electric current is applied to the electrode 200.

The blocking member 400 may be positioned in the outside of the conductive member 300. More particularly, as shown in FIG. 3, the blocking member 400 may cover the outside of the conductive member 300 so that the exposure portion EP is present within the blocking member 400, that is, so that the exposure portion EP is positioned inside the blocking member 400. In an embodiment, the blocking member 400 may be positioned so that the inner surface thereof is in contact with the outer surface of the conductive member 300. Accordingly, the outside moisture or sweat or foreign substances coming from the skin of the user may be prevented from flowing into the electrode.

In an embodiment, the blocking member 400 may be a high molecular compound, as one example, polyurethane.

In an embodiment, the blocking member 400 may include the first blocking portion 410 and the second blocking portion 420.

The first blocking portion 410 is positioned along the outer circumferential surface of the conductive member 300, and at least a portion of the first blocking portion 410 may overlap the conductive member 300 in the first direction (for example, the Z-axis direction of FIG. 3). In an embodiment, the first blocking portion 410 may have a "[" or "]" shape. Also, the first blocking portion 410 is positioned on the outer circumferential surface of the second conductive portion 320 and the top surface of the first conductive portion 310. The first blocking portion 410 extends downward by the height H3 in the height direction (for example, the Z-axis direction of FIG. 3), and thus may be in contact with at least a portion of the outer circumferential surface of the first conductive portion 310.

The second blocking portion 420 may extend outward from one side of the first blocking portion 410 in a radial direction. For example, as shown in FIG. 3, the second blocking portion 420 extends radially outward from an end of the first blocking portion 410 that extends by the height H3, and the second blocking portion 420 may have the height H4.

In an embodiment, at least a portion of the second blocking portion 420 may overlap the absorbent member 500 in the height direction (for example, the Z-axis direction of FIG. 3).

Accordingly, the blocking member 400 is positioned to surround the outer circumferential surface of the conductive member 300, and at least a portion of the blocking member 400 overlaps the conductive member 300 and/or the absorbent member 500 in the first direction. Thus, the outside moisture or foreign substances, or sweat or foreign substances coming from the skin of the user may be prevented from flowing into the electrode 200. Accordingly, it is possible to prevent impedance between the electrode 200 and the electrode 200 from being reduced, thereby enhancing the measurement precision.

In an embodiment, the blocking member 400 may be made of a different material from the conductive member 300. More particularly, the blocking member 400 may be a material having the water absorption rate and impedance different from those of the conductive member 300.

The absorbent member 500 is positioned in the outside of the blocking member 400 and may come into contact with the skin of the user. The absorbent member 500 is a material having excellent moisture absorption and may absorb the outside moisture, sweat on the skin of the user, or the like. For example, the blocking member 500 may be fiber, as one example, nonwoven fabric.

In an embodiment, the absorbent member 500 may be a material having substantially the same moisture absorption as that of the conductive member 300. Here, substantially the same moisture absorption is not intended to represent that the moisture absorption is strictly same, and may encompass unavoidably accompanying engineering tolerance. Accordingly, even if the wearable device 10 has been attached to the skin of the user for a long period of time, regions to which the conductive member 300 and the absorbent member 500 are attached may leave no trace on the skin.

In an embodiment, the absorbent member 500 may be positioned in contact with the outer circumferential surface of the blocking member 400, and may have a height H0. The height H0 may be equal to the height (H1+H2) of the conductive member 300 and/or the height (H3+H4) of the blocking member 400.

In an embodiment, the absorbent member 500 may include a groove (a reference numeral is not shown) formed by partially cutting one surface of the absorbent member 500. More particularly, as shown in FIG. 3, the bottom surface of the absorbent member 500 is partially cut to provide a groove shape, and the second blocking portion 420 may be positioned in the groove.

In an embodiment, the absorbent member 500 includes a membrane having a plurality of pores, and a size of each of the pores may be greater than a size of each of water particles, such as sweat, flowing out from the skin of the user, but less than a size of each of water particles flowing in from the outside. That is, the absorbent member 500 may be a waterproof and moisture-permeable material that allows the sweat coming from the skin of the user to pass therethrough but prevents inflow of the outside water.

Accordingly, in the wearable device 10 according to an embodiment, the conductive member 300 is covered by the blocking member 400, and the outside moisture or sweat or foreign substances of the user is prevented from flowing into the electrode. Thus, it is possible to prevent the impedance between the electrode 200 and the electrode 200 from being reduced. Therefore, the precision of bio signals sensed by the electrode 200 may be improved, and an amount of liquid medicines injected through the skin may be uniformly maintained.

Figure 4:
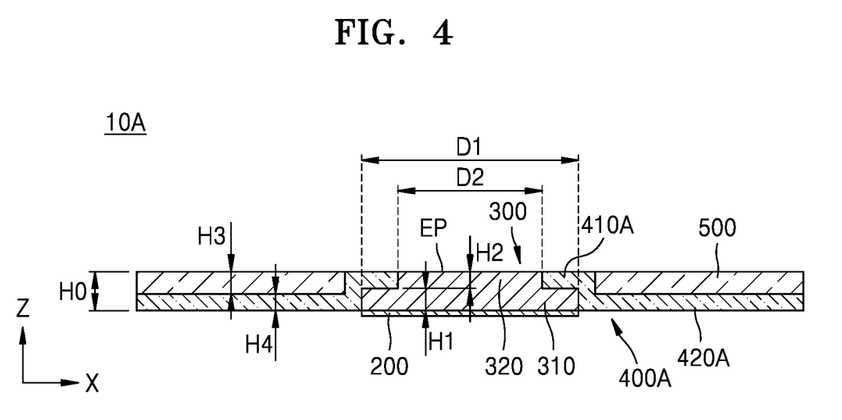
FIG. 4 shows a cross-section of a wearable device according to another embodiment.

FIG. 4 shows a cross-section of a wearable device 10A according to another embodiment.

The embodiment may include a blocking member 400A having a different structure when compared to that of the wearable device 10 according to the embodiment described above. The other components of the embodiment may be the same as the components of the wearable device 10 according to the embodiment described above, and detailed description thereof will be omitted.

As shown in FIG. 4, the blocking member 400A may include a first blocking portion 410A and a second blocking portion 420A.

The first blocking portion 410A may be the same as the first blocking portion 410 described above, and detailed description thereof will be omitted.

The second blocking portion 420A may extend outward from an end of the first blocking portion 410A in a radial direction. In an embodiment, the second blocking portion 420A may be positioned to support the entire bottom surface of an absorbent member 500. That is, the absorbent member 500 is positioned on the second blocking portion 420A and may form a different layer from the second blocking portion 420A.

Through this structure, the wearable device 10A according to the embodiment may more securely prevent moisture, foreign substances, or the like, which have flowed in the absorbent member 500, from flowing into a housing 100.

Figure 5:
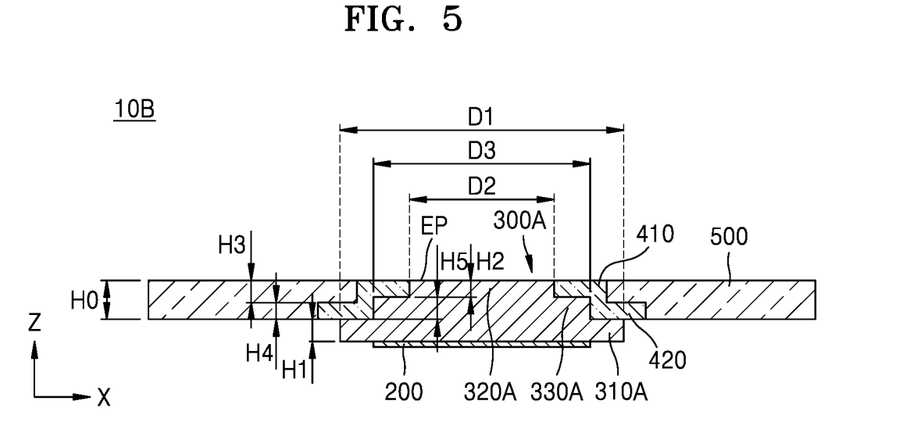
FIG. 5 shows a cross-section of a wearable device according to further another embodiment.

FIG. 5 shows a cross-section of a wearable device 10B according to another embodiment.

The embodiment may include a conductive member 300A having a different structure when compared to that of the wearable device 10 according to the embodiment described above. The other components of the embodiment may be the same as the components of the wearable device 10 according to the embodiment described above, and detailed description thereof will be omitted.

As shown in FIG. 5, the conductive member 300A may include a first conductive portion 310A, a second conductive portion 320A, and a third conductive portion 330A.

The first conductive portion 310A may be positioned on one surface of an electrode 200 and have a first outer diameter D1. In an embodiment, the first conductive portion 310A may be positioned below a blocking member 400 and form a different layer from the blocking member 400. Also, the first outer diameter D1 of the first conductive portion 310A may be greater than the outer diameter of the electrode 200.

The second conductive portion 320A may be positioned concentrically with the first conductive portion 310A and have a second outer diameter D2 less than the first outer diameter D1. In an embodiment, an exposure portion EP may be provided on one surface of the second conductive portion 320A. Also, the second conductive portion 320A may be spaced apart from the first conductive portion 310A in a first direction (for example, the Z-axis direction of FIG. 5).

The third conductive portion 330A may be positioned between the first conductive portion 310A and the second conductive portion 320A. For example, as shown in FIG. 5, the third conductive portion 330A may be positioned concentrically with the first conductive portion 310A and/or the second conductive portion 320A, and have a third outer diameter D3 which is less than the first outer diameter D1 but greater than the second outer diameter D2. Also, the third conductive portion 330A may have a height H5 in the first direction (for example, the Z-axis direction of FIG. 5).

Accordingly, in the wearable device 10B according to the embodiment, the first conductive portion 310A overlaps a second blocking portion 420 in the first direction (for example, the Z-axis direction of FIG. 5) and positioned to cover the top surface of the electrode 200, thus making it possible to prevent the outside moisture, sweat of the user, or the like from flowing in the electrode 200.

Figure 6:
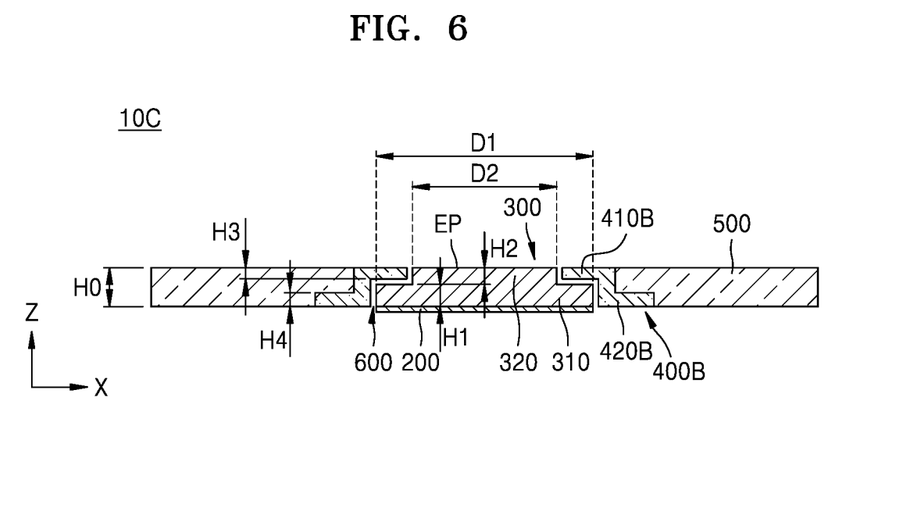
FIG. 6 shows a cross-section of a wearable device according to further another embodiment.

FIG. 6 shows a cross-section of a wearable device 10C according to another embodiment.

The embodiment may include a blocking member 400B having a different structure when compared to that of the wearable device 10 according to the embodiment described above. The other components of the embodiment may be the same as the components of the wearable device 10 according to the embodiment described above, and detailed description thereof will be omitted.

Unlike the embodiment described above, the blocking member 400B may be spaced apart from a conductive member 300. More particularly, as shown in FIG. 6, a first blocking portion 410B may be spaced a predetermined distance from the top surface of a first conductive portion 310 and the outer circumferential surface of a second conductive portion 320. Also, a second blocking portion 420B may extend outward from an end of the first blocking portion 410B in a radial direction and spaced a predetermined distance from the outer circumferential surface of the first conductive portion 310.

Accordingly, a discharge region 600 may be formed between the conductive member 300 and the blocking member 400B. The discharge region 600 may be an empty space defined by the conductive member 300 and the blocking member 400B.

When an excessive amount of moisture is present between the conductive member 300 and the skin of a user, not only may the user feel displeasure while wearing the device, but the device may be detached from the skin. The embodiment may include the discharge region 600 to move and discharge part of moisture or foreign substances, which are present between the conductive member 300 and the skin of the user, through the discharge region 600, thereby preventing the moisture and foreign substances from being locally concentrated on a specific region.

For example, when the wearable device 10C is attached to the skin of the user, a tiny gap may be generated due to the attachment positions and the curve of the skin, part of the moisture or foreign substances, which have flowed in the discharge region 600, may be moved through the gap and then absorbed into the blocking member 400B or an absorbent member 500. Also, the part of the moisture or foreign substances, which have flowed in the discharge region 600, may be moved along the inner wall of a housing 100 and then absorbed into the blocking member 400B or the absorbent member 500.

Figure 7:
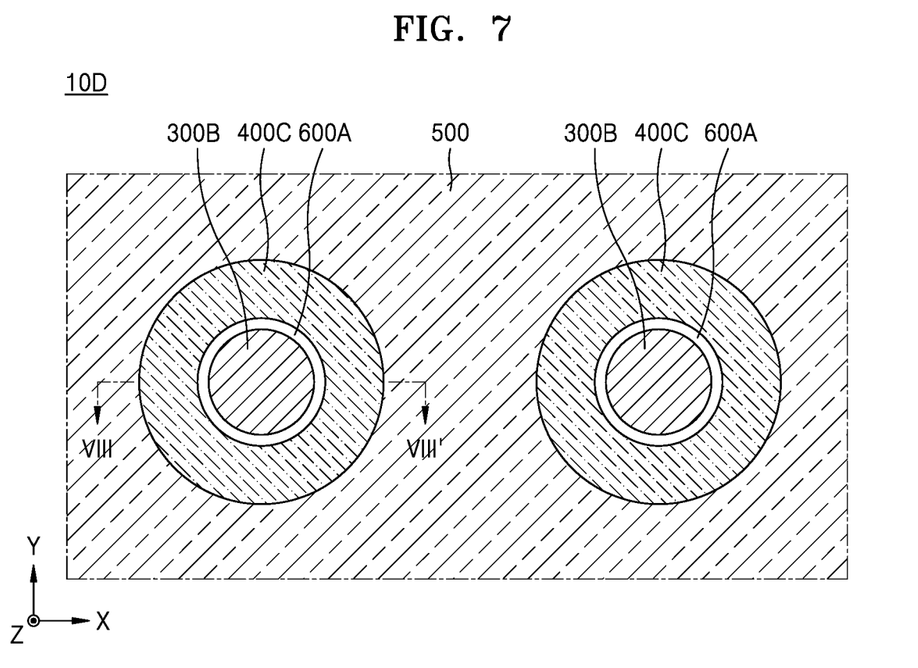
FIG. 7 shows an enlarged view of an electrode of a wearable device according to another embodiment.
Figure 8:
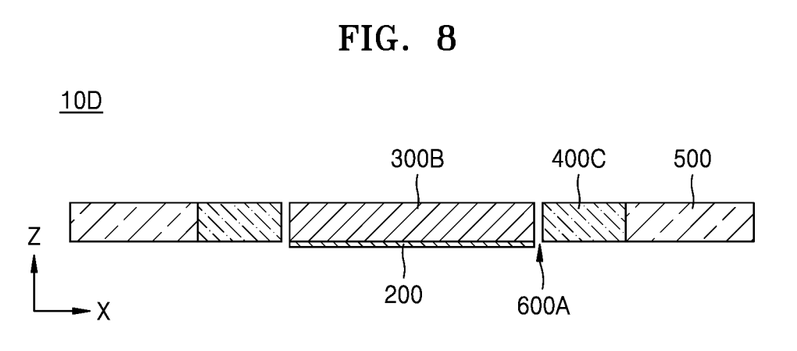
FIG. 8 shows a cross-section of the wearable device taken along line VIII-VIII' of FIG. 7.

FIG. 7 shows an enlarged view of an electrode of a wearable device 10D according to another embodiment, and FIG. 8 shows a cross-section of the wearable device taken along line VIII-VIII' of FIG. 7.

The embodiment may include a conductive member 300B, a blocking member 400C, and a discharge region 600A, which have different structures, when compared to those of the wearable device 10 according to the embodiment described above. The other components of the embodiment may be the same as the components of the wearable device 10 according to the embodiment described above, and detailed description thereof will be omitted.

The conductive member 300B may be positioned on an electrode 200 and include an exposure portion EP that comes into contact with the skin of the user. In an embodiment, the conductive member 300B may have a flat cylindrical shape and made of a single body member instead of a plurality of conductive portions.

The blocking member 400C may have a donut shape with a center hole. More particularly, as shown in FIGS. 7 and 8, the blocking member 400C may be spaced a predetermined distance from the conductive member 300B, and the conductive member 300B may be positioned in the blocking member 400C. Also, the discharge region 600A may be defined in a region in which the conductive member 300B is spaced apart from the blocking member 400C.

In an embodiment, the blocking member 400C may have the same height H0 as the conductive member 300B and/or an absorbent member 500.

In an embodiment, the blocking member 400C may be a nonwoven fabric having the absorption rate and impedance different from those of the absorbent member 500.

In the wearable device 10D according to the embodiment described above, the blocking member 400C and the absorbent member 500 having different moisture absorption are positioned around the electrode 200 and the conductive member 300B. Through this structure, most of the outside moisture or sweat generated from the skin of the user may be absorbed into the absorbent member 500, and only an extremely small amount of the moisture may be absorbed into the blocking member 400C. Accordingly, it is possible to prevent a reduction in the impedance between the electrode 200 and the electrode 200 as much as possible.

Figure 9:
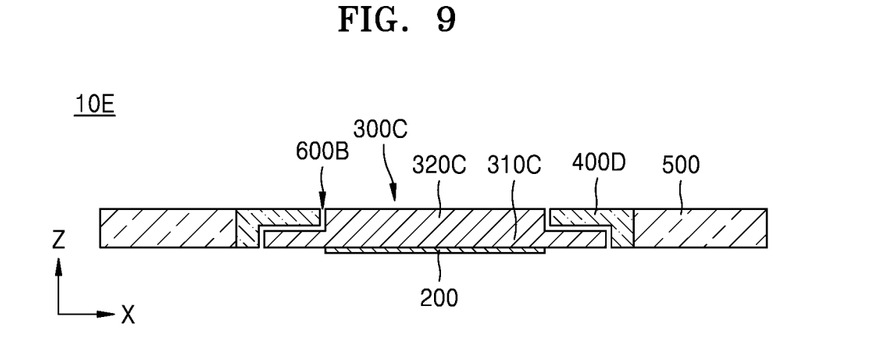
FIG. 9 shows a cross-section of a wearable device according to another embodiment.

FIG. 9 shows a cross-section of a wearable device 10E according to another embodiment.

The embodiment may include a conductive member 300C, a blocking member 400D, and a discharge region 600B, which have different structures, when compared to those of the wearable device 10D according to the embodiment described above. The other components of the embodiment may be the same as the components of the wearable device 10 according to the embodiment described above, and detailed description thereof will be omitted.

The conductive member 300C may include a first conductive portion 310C and a second conductive portion 320C.

The first conductive portion 310C may be positioned on an electrode 200 and have a first outer diameter D1 greater than the outer diameter of the electrode 200. The second conductive portion 320C may be positioned concentrically on the first conductive portion 310C and have a second outer diameter D2 less than the first outer diameter D1.

The blocking member 400D may have a partially cut shape, unlike the blocking member 400C described above. More particularly, as shown in FIG. 9, the blocking member 400D may include a groove (a reference numeral is not shown) formed by cutting a portion of a lower end of the blocking member 400D. A portion of the first conductive portion 310C may be inserted into the groove.

In an embodiment, at least a portion of the blocking member 400D may overlap the first conductive portion 310C in a first direction (for example, the Z-axis direction of FIG. 9). Also, the blocking member 400D may be spaced outward from the conductive member 300C in a radial direction. In addition, the discharge region 600B may be formed in the spaced region.

Accordingly, the discharge region 600B may form much longer channel. Thus, the moisture or foreign substances, which have flowed from the outside or the skin of the user, may stay in the discharge region 600B for a relatively longer period of time and move slowly. Thus, it is possible to prevent the moisture or foreign substances from rapidly moving toward the electrode 200.

The wearable device according to the embodiment may prevent the moisture or foreign substances from flowing in the electrode or positioning around the electrode. Accordingly, the impedance between the electrode and the electrode may be prevented from being reduced by the moisture or foreign substances. Thus, the bio signals of the user may be accurately measured, and a fixed amount of liquid medicines may be injected into the skin of the user at a scheduled time.

Each of the electrode 200, the conductive member 300, and the blocking member 400 has been illustrated as one circular component, but each may have various shapes and may be made by connecting a plurality of components.

The present disclosure has been described with reference to the embodiments illustrated in the drawings, but the embodiments are merely illustrative. It will be understood by those skilled in the art that various modifications and other equivalent embodiments can be made from the embodiments. Hence, the real protective scope of the present disclosure should be determined on the basis of the accompanying claims.

The specific technical features described in the embodiments are merely examples and are not intended to limit the technical scopes of the embodiments. In order to provide concise and clear disclosure, descriptions of general techniques and configurations according to the related art may be omitted. Also, the connecting lines or connecting members between the components illustrated in the drawings represent exemplary functional connections and/or physical or logical connections, and various alternative or additional functional connections, physical connections, or logical connections may be present in a practical device. Also, unless a specific term such as "essential" or "important" is mentioned for a component, the component may not be a necessary component for the application of the present disclosure.

The term "the" or similar references used in the detailed description and claims may cover both the singular and the plural unless specifically limited. Also, if a range is used in the embodiment, the embodiment may be regarded as including the inventive concept in which an individual value belonging to the range is applied (unless otherwise stated), and the individual values constituting the range are written in the detailed description. Unless the order of operations organizing a method according to an embodiment is explicitly mentioned or described otherwise, the operations may be performed in any suitable order. The embodiments are not necessarily limited to the mentioned order of the operations. The use of all examples or exemplary terms (e.g., "etc.", "and (or) the like", and "and so forth") in an embodiment is merely intended to describe the embodiment in detail, and the scope of the embodiment is not limited by the examples or exemplary terms unless defined by the claims. Also, it will be understood by those of ordinary skill in the art that the present disclosure can be made according to design conditions and factors within the range of the claims, in which various changes, combinations, and modifications are added, or an equivalent thereof.

The wearable device according to the embodiment may prevent the sweat, foreign substances, or the like generated from the outside or the skin of the user from flowing in the electrode, thereby preventing the degradation in the quality of signals measured by the electrode.

The wearable device according to the embodiment may prevent the impedance between the electrode and the skin or between the electrode and electrode from being reduced due to the sweat, foreign substances, or the like generated from the outside or the skin of the user, thereby enhancing the measurement precision.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A wearable device adapted to attach to a skin of a user, the wearable device comprising:
   a plurality of electrodes spaced apart from each other;
   conductive members, each positioned on one surface of a respective electrode of the plurality of electrodes and comprises an exposure portion opposite to the respective electrode, wherein each of the conductive members comprises:
      a first conductive portion in contact with the one surface of the respective electrode of the plurality of electrodes and having a first outer diameter; and
      a second conductive portion positioned concentrically with the first conductive portion and having a second outer diameter less than the first outer diameter;
   blocking members, each comprising a different material from the conductive members, and surrounding a respective conductive member so that the exposure portion of the respective conductive member is present therewithin; and
   an absorbent member surrounding the blocking members and adapted to contact the skin of the user;
   wherein each of first conductive portion of the conductive members overlaps with a respective blocking member of the blocking members in a first direction and a portion of each of the blocking members overlaps with the absorbent member in the first direction; and
   wherein none of the conductive members, the blocking members and the absorbent member protrudes further than one another in a direction perpendicular to the one surface of the respective electrode such that the plurality of electrodes, the blocking members, and the absorbent member uniformly come into contact with the skin of the user.

2. The wearable device of claim 1, wherein:

The absorbent member further comprises a membrane having a plurality of pores; and the absorbent member comprises a waterproof and moisture-permeable material and is configured to allow sweat coming from the skin of the user to pass therethrough and prevent inflow of outside water.

3. The wearable device of claim 1, wherein each of the blocking members is positioned concentrically with the respective conductive member and spaced a first distance from each other to define a discharge region.

4. The wearable device of claim 3, wherein the absorbent member is configured to absorb water flowing from the skin of the user and the discharge region is configured to discharge water towards outside.

5. The wearable device of claim 1, wherein each of the conductive members comprises a conductive hydrogel.

6. The wearable device of claim 5, wherein each of the conductive members further comprises a transdermally absorbable drug comprising ionic components.

7. The wearable device of claim 5, wherein each of the conductive members further comprises a chemical substance that contains a transdermally absorbable drug comprising ionic components.

8. The wearable device of claim 1, wherein each of the blocking members further comprises:
a first blocking portion positioned along an outer circumferential surface of the respective conductive member and overlapping the respective conductive member in the first direction; and
a second blocking portion extending outward from one side of the first blocking portion in a radial direction.

9. The wearable device of claim 8, wherein each of the second blocking portion overlaps with the absorbent member in the first direction.

10. The wearable device of claim 8, wherein the absorbent member is positioned on the second blocking portion and forms a different layer from the second blocking portion.

* * * * *